United States Patent [19]

Jellinek

[11] 4,299,919
[45] Nov. 10, 1981

[54] PERFUSATE REDOX POTENTIAL CONTROLLER

[75] Inventor: Max Jellinek, Hazelwood, Mo.

[73] Assignee: St. Louis University, St. Louis, Mo.

[21] Appl. No.: 164,770

[22] Filed: Jun. 30, 1980

[51] Int. Cl.³ ............................................... A01N 1/02
[52] U.S. Cl. ................................. 435/283; 204/195 F; 204/195 L; 204/195 T; 435/1; 435/3; 435/289
[58] Field of Search ....................... 435/1, 3, 283, 289; 128/DIG. 3; 204/195 F, 195 L, 195 T

[56] References Cited

U.S. PATENT DOCUMENTS

| | | | |
|---|---|---|---|
| 3,151,052 | 9/1964 | Arthur et al. | 204/195 T |
| 3,498,888 | 3/1970 | Johansson | 204/195 T |
| 3,753,865 | 8/1973 | Belzer et al. | 435/283 |
| 3,772,153 | 11/1973 | De Roissart | 435/283 |
| 3,892,628 | 7/1975 | Thorne et al. | 435/283 X |
| 3,914,954 | 10/1975 | Doerig | 435/283 X |
| 3,935,065 | 1/1976 | Doerig | 435/283 X |
| 3,995,444 | 12/1976 | Clark et al. | 435/283 X |
| 4,149,950 | 4/1979 | Potts | 204/195 F |
| 4,170,523 | 10/1979 | Buzza et al. | 204/195 T |

OTHER PUBLICATIONS

Codd, Jellinek et al., "Redox Maintenance in Restoration of Organ Viability", 22 Journal of Surgical Research 585–592 (1977).

Primary Examiner—Robert J. Warden
Attorney, Agent, or Firm—Senniger, Powers, Leavitt and Roedel

[57] ABSTRACT

Apparatus for controlling the redox potential of a perfusate for use in the preservation of organs to be transplanted and the like, which apparatus includes first and second cells, a membrane with a submicron pore size disposed in openings between the cells, first and second electrodes disposed in the first and second cells respectively, a reference electrode adapted to be in electrical contact with the perfusate, and circuitry for detecting the redox potential of the perfusate as measured against the reference electrode and for maintaining the redox potential at a predetermined level by causing current to flow between the first and second electrodes through the perfusate when the measured redox potential differs from the predetermined level. The first cell has first and second ports for ingress and egress of the perfusate into and out of the first cell. The membrane allows electrical current to flow between the first and second cells but prevents particles larger than the pore size from passing from one cell to the other.

19 Claims, 3 Drawing Figures

PERFUSATE REDOX POTENTIAL CONTROLLER

BACKGROUND OF THE INVENTION

This invention concerns the preservation of organs for use in transplanting and the like and more particularly concerns apparatus for controlling the redox potential of perfusates used in organ preservation.

A number of methods of organ preservation are available, including inter alia freezing the organ, chilling the organ to a low temperature in a balanced electrolyte bath (hypothermia), storing the organ in an electrolyte bath at normal temperatures with a positive pressure oxygen atmosphere above it (hypobaria), and pumping an oxygenated nutrient medium (a perfusate) through the organ to be preserved (perfusion). Focusing particularly on perfusion, a great deal of work has been done on optimizing various parameters such as temperature, flow rate of the perfusate, perfusate media, and additives to the perfusate. In the course of oxygenating perfusates, the normal oxidation/reduction (redox) potential cannot be maintained without affecting cellular components in the perfusate or in the organ being preserved.

In general, the organ to be preserved is incapable of overcoming the corrosive conditions of its perfusate and as a result develops membrane and mitochondrial damage. For example, hearts removed for preservation are somewhat anoxic. Since biochemical redox reactions are ubiquitous in the cells of the organ and in the reduced state during anoxia, it has generally been thought that extreme alterations in the redox state would not result in pathologic changes in the organ being preserved by perfusion. However, in the extreme anoxic state, hydrogen (which cannot be accepted by pyruvate to form lactate because of system saturation) accumulates, resulting in a redox potential sufficiently low that sulfhydryl linkages are reduced. Breaking the sulfide bridges disrupts the tertiary structure of the proteins, thus modifying or eliminating their function. This event is generally believed to be reversible under ideal conditions. However, rapid reoxygenation of the organ can cause reconnection of the disulfide bridges in incorrect combinations at a time when the cells have no reductive facilities to reverse these mismatches. These incorrect combinations occur soon after the redox potential has shifted from the extreme reduced state to the extreme oxidized state in uncontrolled perfusions. The damage done to the proteins manifests itself in the membrane of each cell, in the sarcoplasmic reticulum, and in the membranes of the mitochondria, thereby causing malfunction of the electron transport system and instability of the lysosomal membrane. It has been suggested, therefore, that the preservation of organs by perfusion could be further improved by maintaining the redox potential of the perfusate at some optimum level. However, apparatus for doing so have suffered from several deficiencies, among them lack of adequate control of the redox potential of the perfusate, insufficient flow rate of the perfusate through the apparatus, complexity of the apparatus, and expense of the apparatus.

SUMMARY OF THE INVENTION

Among the several objects of the present invention may be noted the provision of apparatus which accurately controls the redox potential of a perfusate used in preserving organs for transplant and the like; the provision of such apparatus which has an adequate rate of flow of the perfusate therethrough; the provision of such apparatus which lengthens the time organs may be preserved for transplant over the time resulting from use of previous apparatus; the provision of such apparatus which is simple in construction and in operation; the provision of such apparatus which is simple to disassemble; and the provision of such apparatus which is relatively inexpensive.

Briefly, apparatus of the present invention includes first and second cells, each having an opening for communication of fluid therebetween. The first cell also has first and second ports for ingress and egress of the perfusate into and out of the first cell. The apparatus also includes a membrane disposed in the openings between the first and second cell, which membrane has a submicron pore size whereby electrical current can flow between the first and second cells but particles larger than the pore size cannot. First and second electrodes are disposed in the first and second cells respectively and a reference electrode is adapted to be in electrical contact with the perfusate. Circuitry is included in the apparatus for detecting the redox potential of the perfusate as measured against the reference electrode and for maintaining the redox potential at a predetermined level by causing current to flow between the first and second electrodes through the perfusate when the measured redox potential differs from the predetermined level.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
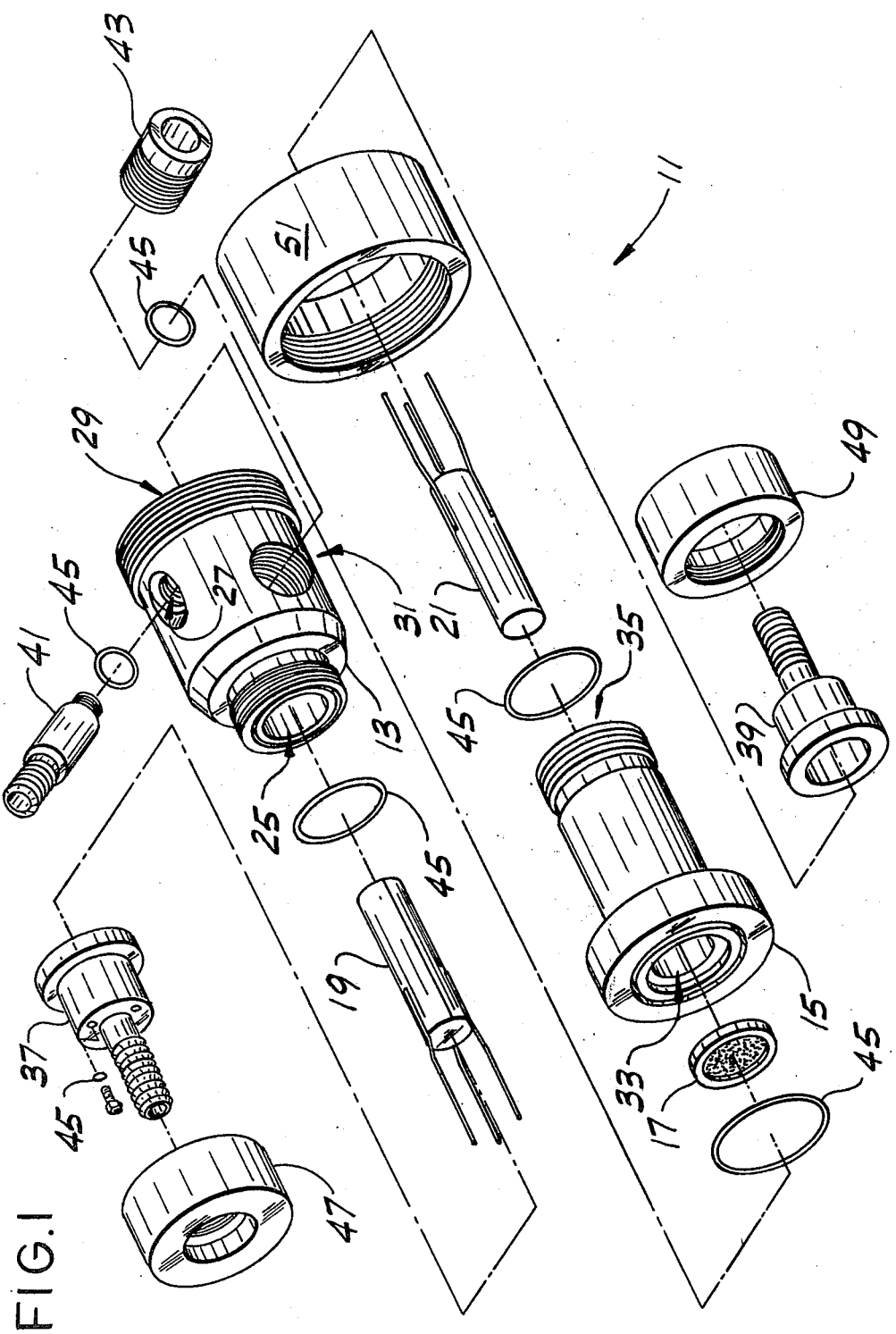
FIG. 1 is an exploded perspective view of the apparatus of the present invention.

Turning to the drawings and more particularly to FIG. 1, apparatus 11 of this invention is shown including a first or working cell 13, a second or auxiliary cell 15, and a membrane 17 such as that sold under the trade designation "Millipore" by the Millipore Corporation of Bedford, Massachusetts. It is preferred that the pore size of membrane 17 be no greater than 0.5 microns. Membranes with a pore size of 0.45 micron have given very satisfactory results. Such a small pore size eliminates having to sterilize cell 15 and has other advantages explained infra. Also shown in FIG. 1 are a first or working electrode 19 and a second or auxiliary electrode 21. The apparatus also includes a silver/silver chloride reference electrode 23 (see FIG. 3).

The working cell includes an ingress port 25 for flow of perfusate into the working cell, an egress port 27 for flow of perfusate out of the working cell, an opening indicated at 29 for communication of fluid between the working and auxiliary cells, and a reference electrode port 31 through which the reference electrode is electrically exposed to the perfusate in the working cell. The axis of the egress port is at an acute angle with respect to the axis of the ingress port because of ease of machining and because it directs the departing flow of perfusate generally back in the same direction as the incoming perfusate. The auxiliary cell has an opening 33 of generally the same size and shape as opening 29 in the working cell for communication of fluid between those two cells and it also has a vent opening or port 35 opposite opening 33 for venting of excess fluid. It is preferred that the perfusate itself include ascorbic acid and glutathione as reducing agents to promote the efficacy of the present invention.

When the apparatus is assembled, a coupling 37 secures working electrode 19 in place inside working cell 13 and provides means for attachment of a hose or the like containing perfusate to the apparatus. Likewise a coupling 39 secures the auxiliary electrode in place inside auxiliary cell 15 and provides means for attachment of a vent hose or tube to the apparatus. A coupling 41 screws into egress port 27 and provides means for attachment to the apparatus of a hose or tube for carrying perfusate away from the working cell. Port 31 is also threaded to receive a fitting 43 for holding the reference electrode. A plurality of O-rings 45 are also included in apparatus 11 to provide watertight seals throughout the apparatus.

In assembling apparatus 11, the three leads of electrode 19 are slid through three corresponding holes of coupling 37 and secured and the three leads of electrode 21 are secured in three holes (not shown) in coupling 39. Coupling 37 is pced in face-to-face abutting relationship with port 25 of the working cell (with an O-ring 45 disposed therebetween) and is secured to the working cell by a nut 47. This causes electrode 19 to be wholly disposed inside cell 13. Likewise, coupling 39 is secured to cell 15 by a nut 49. Coupling 41 and fitting 43 are simply screwed into their respective parts with the O-rings placed as shown. Membrane 17 is placed intermediate cells 13 and 15. More particularly the membrane is placed in the opening that is created by opening 29 of cell 13 and opening 33 of cell 15 when the two cells are placed in face-to-face abutting relationship. The two cells and the membrane disposed therebetween are secured together by a nut 51, along with an O-ring 45 which constitutes means for providing a watertight seal around the membrane whereby fluid passing from one cell to the other must pass through the membrane.

Figure 2:
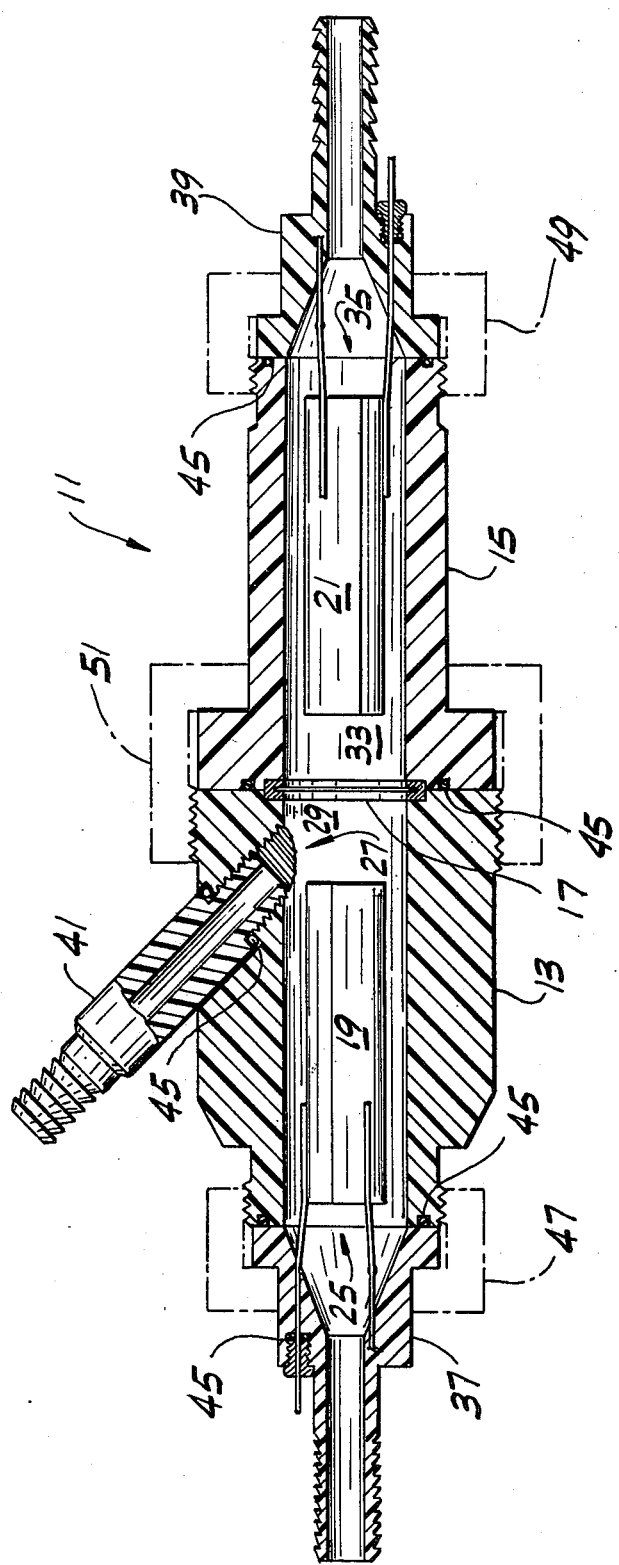
FIG. 2 is a cross-section of the apparatus of the present invention with parts broken away and parts shown in phantom for clarity.

The assembled apparatus is shown in cross-section in FIG. 2. Electrode 19 is disposed in cell 13 adjacent ingress port 25 and coaxial therewith. It is disposed such that perfusate can flow both inside and outside of its generally cylindrical, hollow body. Likewise electrode 21 is coaxial with the vent port and fluid can flow both inside and outside of this electrode in the auxiliary cell. Electrodes 19 and 21 can be platinum or reticulated vitreous carbon. The reticulated vitreous carbon is available from Fluorocarbon, Process Systems Division, of Anaheim, California. It is preferred that the vitreous carbon have a pore size of approximately a millimeter. The body of apparatus 11 is composed of a suitably moldable or machinable plastic. The plastic sold under the trade designation Lexan by General Electric has proved to be satisfactory.

Also shown in FIG. 2 is the fact that the openings in couplings 37 and 39 are generally funnel-shaped near the respective openings or ports of cells 15 and 17. The working and auxiliary electrodes are disposed adjacent the funnel shaped portions of their respective couplings.

Although apparatus 11 is shown in FIGS. 1 and 2 as being secured together with nuts, this need not always be the case. It is preferable that this method of securing be used when the first and second electrodes are platinum because the platinum electrodes are relatively expensive and must be cleaned to be reused. However, when the electrodes are reticulated vitreous carbon (which is many times less expensive than platinum), the apparatus may be in large part injected molded or the like and after use the entire apparatus can be discarded. This provides a better watertight seal since most of the joints and their accompanying O-rings are eliminated.

The electrical circuitry for apparatus 11 (see FIG. 3) includes four RCA Type CA-3140 amplifiers A1-A4, as 20 K-ohm potentiometer R1 used to control the amount of current supplied to electrode 21, an API Instruments Co. Model 7055-4700-0100 D.C. millivolt meter 55 calibrated for the range from −100 millivolt to 0 volts to +100 millivolts, a 2 K-ohm trimmer potentiometer R2 used to calibrate meter 55, a 100 ohm potentiometer R3 which has a precision 10 turn dial calibrated to indicate 0-100 millivolts, a 20 K-ohm trimmer potentiometer R4 which is used to ensure that the total voltage across potentiometer R3 is in fact 100 millivolts, and a switch SW1 which permits selection of the bias polarity of the circuitry. Each amplifier has a 10 K-ohm potentiometer connected between pins 1 and 5, a 521 pF capacitor connected between pins 1 and 8, pin 7 connected to the +15 V supply and pin 4 connected to the −15 V supply. The small triangular symbol represents the circuit common, which is not grounded.

In general amplifier A1 amplifies the signal from the reference electrode, which represents the redox potential of the perfusate in the working cell, and supplies the amplified signal to amplifiers A2 and A4. The output of amplifier A2 is in turn supplied through potentiometer R2 to meter 55, where the actual potential of the perfusate is displayed. Thus, meter 55 constitutes means for displaying the measured redox potential of the perfusate. The output of amplifier A3 is determined by the setting of potentiometer R3 and represents the desired predetermined redox potential level. This output is summed with the output of amplifier A1 and is supplied to the inverting input of amplifier A4. If the potential of the working electrode with respect to the reference electrode (the reference potential) is of the same magnitude as the output of amplifier A3 (the bias potential) but of opposite sign, the output of amplifier A4 is zero; therefore the action of the circuit is to maintain the reference potential at a value equal but opposite to the bias potential. The output of amplifier A4 is in turn supplied through potentiometer R1 to electrode 21 and constitutes the reducing or oxidizing current required to maintain the redox potential at the desired, predetermined level. When a positive potential is required, the arm of switch SW1 contacts the upper, positive contact while when a negative potential is required (which is usually the case) the switch arm is placed in contact with the lower, negative contact. Amplifier A4 constitute means for supplying a reducing current to the working cell when the measured redox potential is above the predetermined level and means for supplying an oxidizing current to the working cell when the measured redox potential is below the predetermined level.

The operation of the apparatus is as follows: Perfusate enters working cell 13 through coupling 37 and port 25, passes in and around working electrode 19, past reference electrode 23, and out of the working cell through port 27 and coupling 41. If the redox potential as measured against the reference electrode is above the desired level, the circuitry of FIG. 3 supplies a reducing current to apparatus 11, causing current to flow between electrodes 19 and 21, and causing reduction to take place at electrode 19 and oxidation to take place at electrode 21 in the auxiliary cell. Because of membrane 17, these oxidation products are generally confined to the auxiliary cell, thereby allowing the net effect on the perfusate of passing through the working cell to be a reduction of the redox potential. On the other hand, if the redox potential measured against the reference electrode is too low, the polarity of the output of the circuitry is reversed and oxidation takes place at electrode 19. In this case, reduction products are confined in the auxiliary cell.

Figure 3:
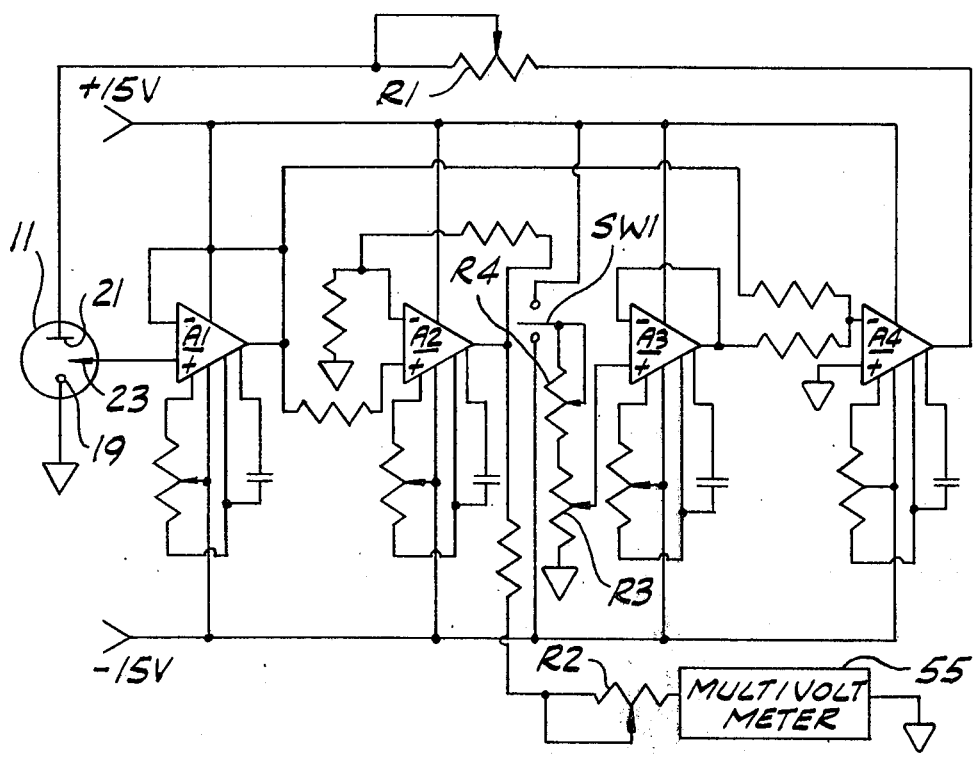
FIG. 3 is a schematic diagram of the electrical circuitry of the present invention.

From the above it can be seen that the circuitry of FIG. 3 constitutes means for detecting the redox potential of the perfusate as measured against the reference electrode and for maintaining said redox potential at a predetermined level by causing current to flow between the first and second electrodes through the perfusate when the measured redox potential differs from the predetermined level. As a result the circuitry also keep the redox ratio of the reducing agents ascorbic acid and glutathione at a predetermined level as well.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. In a perfusion apparatus including an organ chamber, an oxygenator and a pump for pumping a perfusate through the apparatus, the improvement comprising means for controlling the redox potential of the perfusate for use in the preservation of organs comprising:

first and second cells, each having an opening for communication of fluid therebetween, said first cell also having first and second ports for ingress and egress of the perfusate into and out of said first cell;
   a membrane disposed in the openings between the first and second cells, said membrane having a submicron pore size, whereby electrical current can flow between the first and second cells but particles larger than the pore size cannot;
   first and second electrodes disposed in the first and second cells respectively;
   a reference electrode adapted to be in electrical contact with the perfusate; and
   means for detecting the redox potential of the perfusate as measured against the reference electrode and for maintaining said redox potential at a predetermined level by causing current to flow between the first and second electrodes through said perfusate when the measured redox potential differs from the predetermined level.

2. Apparatus as set forth in claim 1 wherein the first and second cells are disposed adjacent each other with their respective openings in abutting relationship, further including means for providing a watertight seal around the membrane whereby fluid passing from one cell to the other must pass through the membrane.

3. Apparatus as set forth in claim 1 wherein the second cell has a port for use as a vent.

4. Apparatus as set forth in claim 3 wherein the second electrode is disposed adjacent said port in the second cell.

5. Apparatus as set forth in claim 4 wherein the second electrode is coaxial with said port in the second cell.

6. Apparatus as set forth in claim 1 wherein the first electrode is disposed adjacent the ingress port of the first cell and coaxial therewith.

7. Apparatus as set forth in claim 1 wherein the axis of the egress port is at an acute angle with respect to the axis of the ingress port.

8. Apparatus as set forth in claim 1 wherein the first electrode has a cylindrically shaped body.

9. Apparatus as set forth in claim 8 wherein the first electrode is disposed so that during operation the perfusate flows both inside and outside the cylindrically shaped electrode body.

10. Apparatus as set forth in claim 8 wherein the first electrode is composed of a material selected from the group consisting of platinum and reticulated vitreous carbon.

11. Apparatus as set forth in claim 1 wherein the reference electrode is partially disposed in the first cell whereby the redox potential detected by the detecting and maintaining means is the potential of the perfusate in the first cell.

12. Apparatus as set forth in claim 11 wherein the reference electrode is a silver/silver chloride electrode.

13. Apparatus as set forth in claim 1 wherein the pore size of the membrane is no greater than 0.5 microns.

14. Apparatus as set forth in claim 13 wherein said pore size is 0.45 microns.

15. Apparatus as set forth in claim 1 wherein the second electrode has a cylindrically shaped body.

16. Apparatus as set forth in claim 1 wherein the second electrode is composed of a material selected from the group consisting of platinum and reticulated vitreous carbon.

17. Apparatus as set forth in claim 1 wherein the detecting and maintaining means includes means for supplying a reducing current to the first cell when the measured redox potential is above the predetermined level.

18. Apparatus as set forth in claim 1 wherein the detecting and maintaining means includes means for supplying an oxidizing current to the first cell when the measured redox potential is below the predetermined level.

19. Apparatus as set forth in claim 1 further including means for displaying the measured redox potential of the perfusate.

* * * * *